United States Patent [19]

Graff et al.

[11] Patent Number: 5,050,703
[45] Date of Patent: Sep. 24, 1991

[54] ELECTRODYNAMIC TRANSDUCER HEAD

[75] Inventors: Alfred Graff, Essen; Friedhelm Schlawne, Kerpen; Michael Wächter, Ratingen; Wolfgang Böttger, Düsseldorf, all of Fed. Rep. of Germany

[73] Assignee: Mannesmann Aktiengesellschaft, Düsseldorf, Fed. Rep. of Germany

[21] Appl. No.: 417,329

[22] Filed: Oct. 5, 1989

[30] Foreign Application Priority Data

Oct. 5, 1988 [DE] Fed. Rep. of Germany ....... 3834248

[51] Int. Cl.$^5$ ............................................ G01N 29/04
[52] U.S. Cl. ........................................ 181/106; 73/643
[58] Field of Search ................. 181/106, 208; 73/643, 73/576, 578, 668

[56] References Cited

U.S. PATENT DOCUMENTS

| | | | |
|---|---|---|---|
| 4,296,486 | 10/1981 | Vasile | 73/643 |
| 4,480,477 | 11/1984 | Huschelrath et al. | 73/643 |
| 4,578,999 | 4/1986 | Abend et al. | 73/643 |
| 4,596,147 | 6/1986 | Behl et al. | 73/643 |
| 4,602,175 | 7/1986 | Castagna | 336/208 |
| 4,602,512 | 7/1986 | Kowol et al. | 73/643 |
| 4,665,752 | 5/1987 | Huschelrath et al. | 73/643 |

FOREIGN PATENT DOCUMENTS 2006433  5/1979  United Kingdom .............. 73/576

OTHER PUBLICATIONS

Maxfield et al; "Design of Permanent Magnet . . . "; 1976 Ultrasonics Symp. Proc., pp. 22–25.

Primary Examiner—Nelson Moskowitz
Attorney, Agent, or Firm—Horst M. Kasper

[57] ABSTRACT

The invention furnishes an electrodynamic transducer head for a non-destructive testing of workpieces with electrically conductive surfaces by way of ultrasound. A magnet system is employed for generating of a static or a low-frequency magnet field, and at least one transducer coil is disposed at the front face of the magnet system disposed toward the workpiece. The transducer coil is furnished on the side toward the workpiece with a wear-resistant layer, and the transducer coil exhibits between itself and this front face of the magnet system an intermediate part with an insulating layer, which is solidly connected with the front face and with the coil adjoining at the insulating layer. The invention discloses production of a transducer coil, in a way which is simple and economical and results in a transducer head which can be universally employed, and where the eddy current formations, resulting in interfering signals, and the mechanical vibrations, both in the transducer coil as well as in the magnet system, are substantially suppressed or, respectively, damped. The intermediate part (10) comprises at least two layers (11, 12), where one of the layers (12) is electrically conductive and which layer (12) is made of a material thickness which is larger than the skin depth for a given high-frequency field.

28 Claims, 3 Drawing Sheets

ELECTRODYNAMIC TRANSDUCER HEAD

BACKGROUND OF THE INVENTION

1. Field of the Invention

The invention relates to an electrodynamic transducer head for a non-destructive testing of workpieces with electrically conductive surface by way of ultrasound, where a magnet system is employed for generating of a static or low-frequency magnetic field, and where a transducer coil is disposed at a front face of the magnet system, disposed toward the workpiece.

2. Brief Description of the Background of the Invention Including Prior Art

A corresponding electrodynamic transducer head is taught in British Patent GB 2,006,433. The transducer head, provided with an electromagnet, exhibits an annular-shaped outer pole shoe and an inner pole shoe, disposed coaxially relative to the outer pole shoe. This inner pole shoe comprises also two sections, disposed coaxially relative to each other, which sections can be displaced in axial direction relative to each other. The emitter and receiver coils are disposed at the front face of the inner pole shoe disposed toward the workpiece to be tested. In order to avoid mechanical destruction of these sensitive parts by the workpiece, the emitter and receiver coils are covered on the workpiece side with a ceramic layer. An intermediate part with an insulating layer is disposed between the side of the transducer coils facing the pole and the front face of the magnet. The intermediate part with the insulating layer is solidly connected with the front face of the electromagnet and with the coil adjoining the insulating layer. This proposed transducer head is not suitable for all fields of application, in particular as far as the use of a permanent magnet is concerned. In addition, this arrangement does by no means suppress the eddy current formation in the pole shoe. Further, this arrangement is not suitable to damp the mechanical vibrations of the transducer coils themselves or, respectively, the propagation of ultrasound in the magnet. The ultrasound interference signals originating from the pole shoe, which ultrasound interference signals are based on the not purposely suppressed ultrasound interference excitations in the magnet pole shoe, interfere with the evaluation of the incoming signals, and the presence of insufficiently damped vibrations of the transducer coil system increases the non-usable dead time of the amplifier electronics.

SUMMARY OF THE INVENTION

1. Purposes of the Invention

It is an object of the present invention to provide an improved electrodynamic transducer head which can be produced in a simple and economic way and which can be universally employed.

It is another object of the present invention to provide an improved electrodynamic transducer head, where eddy current formations and mechanical vibrations, resulting in erroneous signals, are substantially suppressed or, respectively, damped both in the magnet system as well as in the transducer coil.

It is yet another object of the present invention to produce an electrodynamic transducer head, which is capable of suppressing interference signals.

These and other objects and advantages of the present invention will become evident from the description which follows.

2. Brief Description of the Invention

The present invention provides for an electrodynamic transducer head for non-destructive testing of workpieces having an electrically conductive surface. A magnet system, having a front face disposed on the side of the magnet system toward the workpiece, generates a quasistatic magnet field. A transducer coil is disposed at said front face of the magnet system. Said transducer coil generates ultrasound signals and exhibits a wear-resistant layer on the side disposed toward the workpiece. An insulating layer and an electrically conductive layer form an intermediate part. The intermediate part is disposed between the transducer coil and said front face of the magnet system. The intermediate part is associated with the transducer coil. The intermediate part is solidly connected with said front face and with the transducer coil adjoining at the insulating layer. The thickness of the material of the electrically conductive layer is larger than the skin depth of an electromagnetic field for a given high-frequency of the electromagnetic field.

The insulating layer can be made of a plastic. The plastic layer can be formed as a foil. The plastic layer can be made of a hardenable casting mass. The plastic layer can be formed by one or more layers of an adhesive. The transducer coil can be embedded in a castable plastic mass.

The electrically conductive layer can be made of an electrically conductive material. The electrically conductive layer, made of copper, can be formed as a thin-walled foil. The foil can exhibit several parallel-disposed slots. The electrically conductive layer can be a copper layer and can be formed as a wire netting or gauze wire. The distance of the electrically conductive layer made of copper relative to the transducer coil can be larger than 0.2 mm. The intermediate space between electrically conductive layer and transducer coil can be filled with plastic. The intermediate part can be formed of several layers connected to each other.

The magnet system can be formed as an electromagnet or as a permanent magnet. The permanent magnet can be formed of a neodymium-iron-boron Nd-Fe-B material.

The transducer coil can be furnished as a coil system with separately disposed receiver and emitter coils.

A non-destructive testing method for workpieces having an electrically conductive surface comprises the following steps. A workpiece, having an electrically conductive surface, is placed adjacent to a magnet system. Said magnet system, having a front face disposed on the side of the magnet system toward the workpiece, generates a quasi-static magnet field. A transducer coil, disposed at said front face, is protected with a wear-resistant layer on the side disposed toward the workpiece. High frequency pulses are fed to the transducer coil. Ultrasound signals are generated with the transducer coil. Parasitic ultrasound-wave excitations are damped with an insulating layer and an electrically conductive layer. The insulating layer and the electrically conductive layer form an intermediate part. Said intermediate part is disposed between the transducer coil and said front face of the magnet system. The intermediate part is associated with the transducer coil. The intermediate part is solidly connected with said front face and with the transducer coil adjoining at the insulating layer. The thickness of the material of the electrically conductive layer is larger than the skin depth of an electromagnetic field for a given high-frequency of the electromagnetic field. A reflected signal is received from the workpiece with a receiver coil.

The mode of operation and the the construction of electrodynamic transducer heads have been described extensively in the prior art. These transducer heads consist substantially of a transducer coil or, respectively, a coil system with various separately disposed emitter and receiver coils. The emitter and receiver coils are disposed in a static or, respectively, low-frequency magnetic field opposite to the workpiece and close to the surface of the workpiece. The transducer coil is furnished with high-frequency pulses and generates thereby ultrasound pulses in the workpiece. The receiving of the reflected ultrasound waves from the test piece is performed according to a reciprocal mechanism. However, since the reflection or echo signal is very small as compared to the standard piezoelectric method with a direct contact, on the one hand, the sensing circuit for the echo signal has to be very sensitive and, on the other, the transducer coil has to be disposed as close as possible to the surface of the workpiece to be tested. The test result is furthermore limited in that interfering signals, generated by parasitic ultrasound wave excitation in the magnet system, occur in the same order of magnitude as the test signals and cannot be accurately distinguished from the test signals.

In addition, the non-usable dead zone is increased if mechanical vibrations are generated based on the application of high-frequency to the exciter coils or, respectively, by alternating interaction of the coils with each other.

According to the present invention an intermediate part, comprised of at least two layers, is employed and disposed between the transducer coil and the magnet system. The intermediate part suppresses, on the one hand, the eddy current excitations in the magnet system and, on the other hand, the mechanical vibrations in the coil system. Advantageously, one layer of the intermediate part is electrically conductive, for example, as provided in form of a thin copper foil, whereas the second layer is made of plastic. The thickness of the copper foil depends on the frequency of the applied high-frequency field and is to be larger than the skin depth. For example, for high-frequency fields of 3 MHz, the skin depth amounts to 38 micrometers. In such a case, the thickness of the copper foil would be selected in the region of about 0.1 mm. The copper foil is extraordinarily well suited to prevent an eddy current excitation in the magnet system. For improving the mode of operation, it is furthermore disclosed to furnish the copper foil with several parallel-disposed slots or, alternatively, to furnish a copper shielding in the form of a gauze wire or wire netting. Based on the shielding, there are generated ultrasound wave excitations in the copper foil, which ultrasound wave excitations can be suppressed by the second layer of the intermediate part made of plastic. This plastic layer can furthermore be provided in the form of a thin foil or, advantageously, as a hardenable casting mass. The casting in addition opens up the possibility to embed the transducer coils or, respectively, the complete coil system together with the cast plastic, in order to suppress the interfering interactions of the component with each other. Alternatively, the damping plastic layer can also be comprised of one or several layers of an applied plastic adhesive.

In order to increase the shielding and damping effects, the intermediate part can comprise several layers connected to each other, wherein at least one layer of these layers is electrically conductive.

A conventional permanent magnet or an electromagnet is employed as the magnet system. In the case of the use of an electromagnet, sheet-metal or, respectively, slotted pole shoes are frequently employed in order to suppress the eddy current excitations, as taught in German Patent Application DE 3,401,072. The application of the proposed intermediate part, however, is more advantageous relating to production technology and relating to cost, as compared to the conventional structure. In contrast to the slotted pole shoes, the magnet field also remains without influence upon application of such a disclosed intermediate part. However, the use of an intermediate part is associated with particularly advantageous properties when the transducer head is provided with a permanent magnet system. By using a permanent magnet, the electrodynamic transducer head can be formed particularly small, which is of advantage in many exceptional application cases. The conventional permanent magnet materials allow only a limited mechanical machining such that ultrasound interference signals in this case can only be suppressed by the intermediate part according to the present invention.

Depending on the application, the electrodynamic transducer head can be shaped differently, for example, as an angular test probe. In this case, the emitter or, respectively, receiver coils are disposed at approximately the same distance relative to the magnet system as well as to the test piece. In case of insufficient shielding of the magnet system, there can result comparably strong ultrasound excitation in the magnet system as compared to the test piece itself, and thus there results a receiving of correspondingly sized interference signals. The invention construction of a copper foil between the transducer coil and the magnet system effects a shielding of the magnet system against the high-frequency currents of the exciter coils. Eddy currents are excited exclusively in the copper foil in case of a corresponding thickness of the copper foil, from about 0.05 mm to 0.1 mm, at an excitation frequency of from 1 MHz to 2 MHz.

Based on the arrangement of the coils of the angular test probe, there can be generated and excited planar waves in the copper foil, which planar waves are also received as interference signals. For this purpose, a strong sound-damping plastic layer is applied on the copper foil on the coil side, which sound-damping plastic layer suppresses the propagation of planar waves in the copper foil.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1:
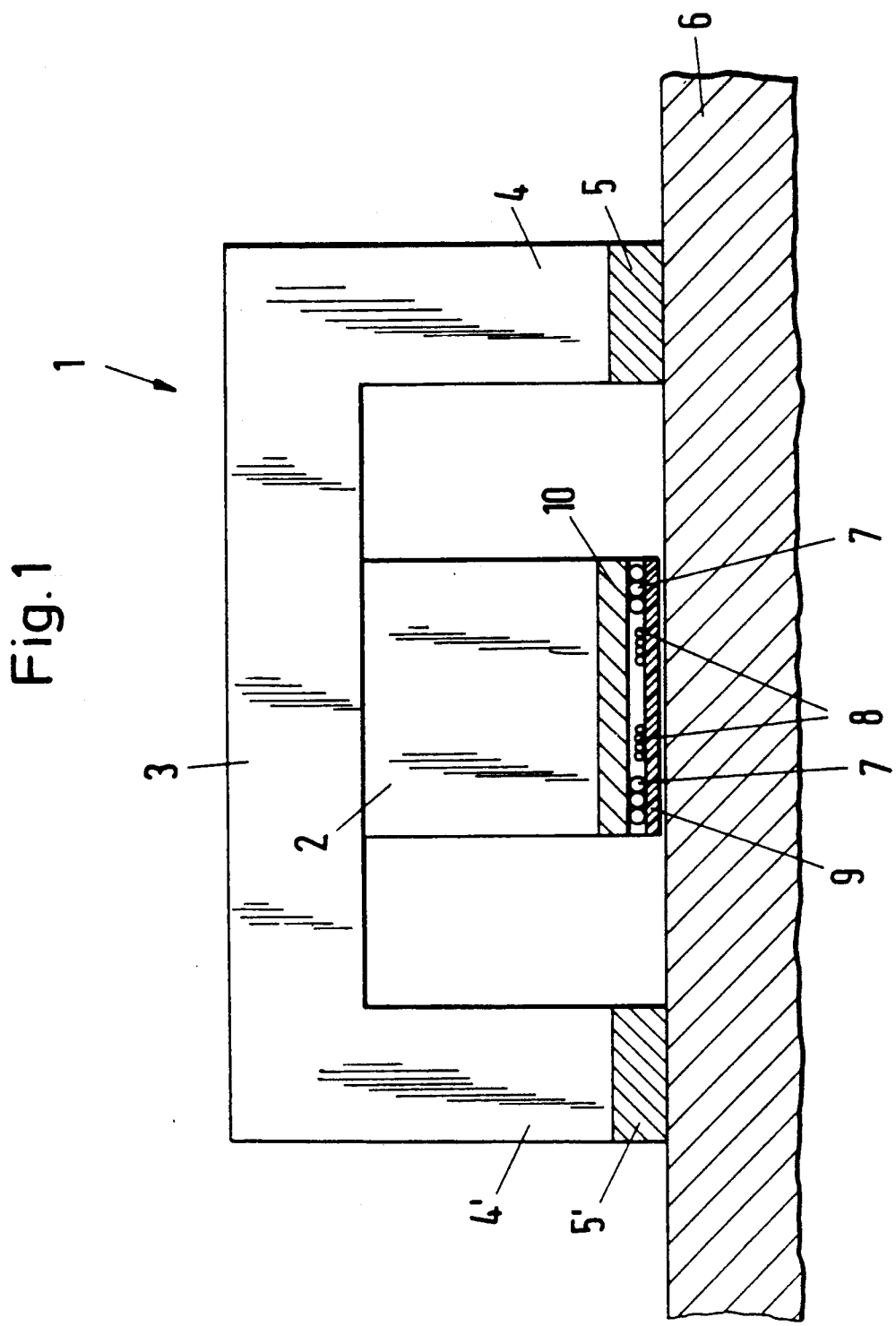
FIG. 1 shows a schematic longitudinal section through a transducer head.

In accordance with the present invention, there is provided an electrodynamic transducer head for nondestructive testing of workpieces with electrically conductive surface by way of ultrasound. A magnet system generates a static or low-frequency magnet field. At least one transducer coil is disposed at the front face of the magnet system toward the workpiece. Said transducer coil exhibits, on the side disposed toward the workpiece, a wear-resistant layer. An intermediate part 10 is formed of at least two layers 11, 12. A first layer 11 of the two layers is an insulating layer and a second layer 12 of the two layers is electrically conductive. Said intermediate part is disposed between the transducer coil and said front face of the magnet system and is associated with the transducer coil. The intermediate part is solidly connected with said front face and with the transducer coil adjoining at the insulating layer. The thickness of the material of the electrically conductive layer is larger than the skin depth for a given high-frequency field.

One of the layers can be made of a plastic and be formed as a foil. One of the layers can be a plastic layer and be made of a hardenable casting mass. The transducer coil can be embedded in a castable plastic mass. The plastic layer can also be formed by one or more layers of an adhesive.

The electrically conductive layer 12 can be made of copper and be formed as a thin-walled foil exhibiting several parallel-disposed slots. The electrically conductive layer can be a copper layer and can be formed as a wire netting or gauze wire. The distance of the electrically conductive layer, made of copper, relative to the transducer coil 7, 8 can be larger than 0.2 mm and the intermediate space 13 can be filled with plastic.

The intermediate part can also be formed of several layers connected to each other.

The magnet system can be formed as an electromagnet. The magnet system can also be formed as a permanent magnet made of a neodymium-iron-boron Nd-Fe-B material.

The transducer coil can be furnished as a coil system with separately disposed receiver and emitter coils.

According to this example, the transducer head 1 comprises an electromagnet system with a permanent magnet 2 and a U-shaped flux return 3. Hard-metal parts forming pole-shoe ends 5, 5' are disposed at the ends 4, 4' of the flux return 3 for protection against wear. Thus, the transducer head 1 can be applied to and can be contacted directly by the workpiece 6 to be tested. The magnet system generates a static or a low frequency magnetic field. For purposes of the invention, a low-frequency magnetic field has a frequency of less than 1000 Hz and preferably of less than 100 Hz, and more preferably of less than 20 Hz. A quasi-static magnetic field is a low-frequency magnetic field or a static magnetic field. The coil system, disposed at an end of the permanent magnet 2, comprises here separately disposed emitter coil 7 and receiver coil 8 and is furnished on the workpiece side with a non-conductive wear-resistant layer 9. The emitter coil can also be designated as transducer coil or exciter coil. The receiver coil can also be designated as transducer coil. This wear-resistant layer 9 can be furnished, for example, by way of a ceramic or a plastic plate. According to the invention, the intermediate part 10 is solidly connected with the permanent magnet 2 on the side disposed toward the permanent magnet 2.

Figure 2:
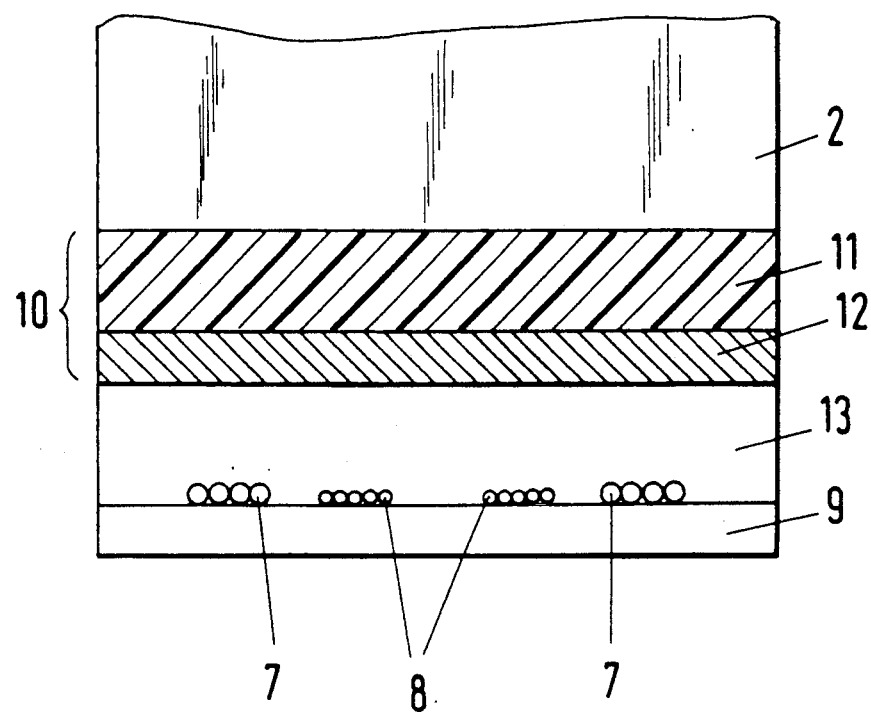
FIG. 2 illustrates the intermediate part according to the invention, at an enlarged scale.
Figure 3:
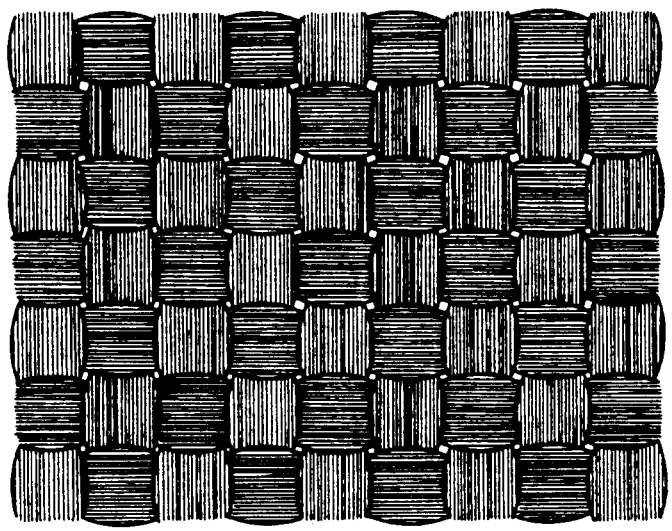
FIG. 3 is a diagram of a metal foil formed of a woven material.
Figure 4:
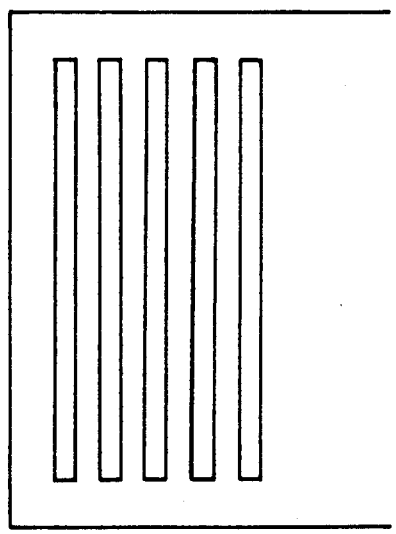
FIG. 4 illustrates an embodiment of the metal foil with parallel-disposed slots.
Figure 5:
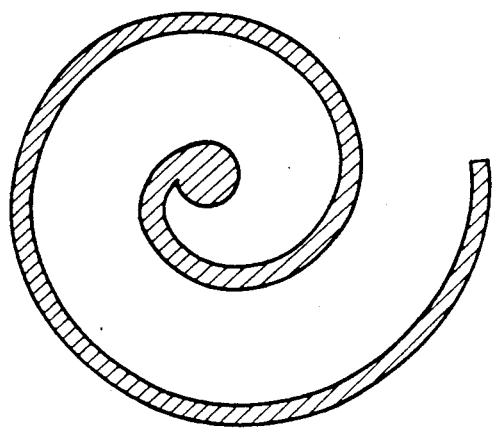
FIG. 5 illustrates an embodiment of the metal fabric shaped as a spiral.

The invention intermediate part 10 is illustrated in FIG. 2 at an enlarged scale. According to this embodiment, the intermediate part 10 includes a conductive shielding layer 12 for the eddy current excitation provided by a copper foil. The copper foil is disposed in the direction of the magnet 2 at a defined distance relative to the emitter coil 7 and the receiver coil 8. The thereby resulting intermediate space 13 is filled with a casting mass made of a castable plastic. The interfering interactions of the parts among each other can be suppressed with the embedding of the transducer coils 7, 8. The second layer of the intermediate part 10 is formed as a damping plastic layer 11, which is disposed between the copper foil and the permanent magnet 2. The ultrasound waves, generated by the shielding effect in the copper foil, can be damped substantially in the layer 11.

Preferably, the receiver coil 8 is disposed inside of an annular area formed by the emitter coil 7. The plastic layer 11, disposed between the magnet 2 and the conductive shielding layer 12, can have a thickness which is from about 1.2 to 3 times, and preferably from about 1.8 to 2.2 times, the thickness of the conductive shielding layer 12. The wear-resistant layer 9 can have a thickness of from about 0.5 to 1.5, and preferably of about 0.8 to 1.2, times the thickness of the conductive shielding layer 12. The distance of the receiver and/or emitter coil 7, 8, from the surface of the conductive shielding layer 12 and/or the thickness of the casting mass can be from about 0.5 to 5.0 times, and preferably from about 1.5 times to 2.5 times, the thickness of the conductive shielding layer 12. The outer diameter of the conductive shielding layer 12 can be from about 1.1 to 1.6, and preferably from about 1.25 to 1.4, times the maximum of the outer diameter of the emitter coil 7 and the receiver coil 8. The disposition of the wear-resistant layer 9 is preferably recessed relative to the position of the wear-resistant pole shoe ends 5, 5' as to their relative planar position, and such recess can correspond to about 0.2 to 1.0 times and preferably from about 0.3 to 0.7 times the thickness of the conductive shielding layer.

It will be understood that each of the elements described above, or two or more together, may also find a useful application in other types of electromagnetic and ultrasound test systems differing from the types described above.

While the invention has been illustrated and described as embodied in the context of a an electrodynamic transducer head, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An electrodynamic transducer head for non-destructive testing of workpieces having an electrically conductive surface comprising
   a rare earth alloy magnet system, having a front face disposed on the side of the magnet system toward the workpiece, for generating of a quasi-static magnet field;
   an insulating layer adjoining at a first side the front face of the magnet system;
   an electrically conductive shielding layer, adjoining at a first side of the insulating layer wherein the insulating layer and the electrically conductive layer form an intermediate part, and wherein the intermediate part is disposed between the transducer coil and said front face of the magnet system, and wherein the intermediate part is associated with the transducer coil, wherein the intermediate part is soildly connected with said front face and with the transducer coil adjoining at the insulating layer, and wherein the thickness of the material of the electrically conductive layer is larger than the skin depth of an electromagnetic field for a given high-frequency of the electromagnetic field;
   a casting layer made of a castable plastic and adjoining with one end a second face of the electrically conductive layer;
   a first transducer coil embedded within said casting layer for generating ultrasound signals with the transducer coil;
   a second transducer coil dispersed substantially concentric to the first transducer coil for picking up reflected signals.

2. The transducer head according to claim 1, wherein the insulating layer is made of a plastic.

3. The transducer head according to claim 2, wherein the plastic layer is formed as a foil.

4. The transducer head according to claim 1 further comprising
   a wear resistant layer, adjoining a second side of the casting layer next to the transducer core to protect against wear.

5. The transducer head according to claim 2, wherein the plastic layer is formed by one or more layers of an adhesive.

6. The transducer head according to claim 1, wherein the transducer coil is embedded in a castable plastic mass.

7. The transducer head according to claim 1, wherein the electrically conductive layer is made of an electrically conductive material.

8. The transducer head according to claim 1, wherein the electrically conductive layer is made of copper.

9. The transducer head according to claim 8, wherein the electrically conductive layer, made of copper, is formed as a thin-walled foil.

10. The transducer head according to claim 9, wherein the foil exhibits several parallel-disposed slots.

11. The transducer head according to claim 8, wherein the electrically conductive layer is a copper layer and is formed as a wire netting or gauze wire.

12. The transducer head according to claim 8, wherein the distance of the electrically conductive layer made of copper relative to the transducer coil is larger than 0.2 mm and wherein the intermediate space between electrically conductive layer and transducer coil is filled with plastic.

13. The transducer head according to claim 1, wherein the intermediate part is formed of several layers connected to each other.

14. The transducer head according to claim 1, wherein the magnet system is formed as an electromagnet.

15. The transducer head according to claim 1, wherein the magnet system is formed as a permanent magnet.

16. The transducer head according to claim 15, wherein the permanent magnet is formed of a neodymium-iron-boron Nd-Fe-B material.

17. The transducer head according to claim 1, wherein the transducer coil is furnished as a coil system with separately disposed receiver and emitter coils.

18. An electrodynamic transducer head for non-destructive testing of workpieces with electrically conductive surface by way of ultrasound, comprising
   a rare earth alloy magnet system for generating of a static or low-frequency magnet field;
   at least one transducer coil disposed at the front face of the magnet system toward the workpiece, which transducer coil exhibits, on the side disposed toward the workpiece, a wear-resistant layer;
   an intermediate part (10) formed of at least two layers (11, 12), wherein a first layer (11) of the two layers is an insulating layer and wherein a second layer (12) of the two layers is electrically conductive, said intermediate part being disposed between the transducer coil and said front face of the magnet system and being associated with the transducer coil, which intermediate part is solidly connected with said front face via said second layer and via an intermediate space filled by a casting mass and with the transducer coil adjoining at the insulating layer, and where the thickness of the material of the electrically conductive layer is larger than the skin depth for a given high-frequency field.
   a second transducer coil dispersed substantially concentric to the first transducer coil for picking up reflected signals.

19. The transducer head according to claim 18, wherein one of the layers ia made of a plastic and formed as a foil.

20. The transducer head according to claim 18, wherein one of the layers is a plastic layer and made of a hardenable casting mass; and wherein the transducer coil is embedded in a castable plastic mass.

21. The transducer head according to claim 18, wherein
   one of the layers is a plastic layer formed by one of more layers of an adhesive.

22. The transducer head according to claim 18, wherein the electrically conductive layer (12) is made of copper and formed as a thin-walled foil exhibiting several parallel-disposed slots.

23. The transducer head according to claim 18, wherein the electrically conductive layer is a copper layer and is formed as a wire netting or gauze wire;
   wherein the distance of the electrically conductive layer, made of copper, relative to the transducer coil (7, 8) is larger than 0.2 mm and the intermediate space (13) is filled with plastic;
   wherein the intermediate part is formed of several layers connected to each other.

24. The transducer head according to claim 18, wherein the magnet system is formed as an electromagnet.

25. The transducer head according to claim 18, wherein the magnet system is formed as a permanent magnet made of a neodymium-iron-boron Nd-Fe-B material.

26. The transducer head according to claim 18, wherein the transducer coil is furnished as a coil system with separately disposed receiver and emitter coils.

27. An electrodynamic transducer head for non-destructive testing of workpieces with electrically conductive surface by way of ultrasound, including a rare earth alloy magnet system for generating of a static or low-frequency magnet field and at least one transducer coil disposed at the front face of the magnet system toward the workpiece, which transducer coil exhibits, on the side disposed toward the workpiece, a wear-resistant layer, and which transducer coil is associated with an intermediate part with an insulating layer disposed between the transducer coil and said front face of the magnet system, which intermediate part is solidly connected with said front face and with the transducer coil adjoining at the insulating layer, the improvement comprising that the intermediate part (10) is formed of at least two layers (11, 12), wherein one layer (12) of the two layers is electrically conductive, wherein the transducer coil is disposed adjacent to the electrically conductive layer, and wherein the transducer coil is solidly mounted to the metallic layer via an intermediate space filled with a casting mass and where the thickness of the material of the electrically conductive layer is larger than the skin depth for a given high-frequency field;

a second transducer coil dispersed substantially concentric to the first transducer coil for picking up reflected signals.

28. A non-destructive testing method for workpieces having an electrically conductive surface comprising placing a workpiece, having an electrically conductive surface, adjacent to a rare earth alloy magnet system, said magnet system having a front face disposed on the side of the magnet system toward the workpiece, for generating of a quasi-static magnet field, and having a transducer coil disposed at said front face and protected with a wear-resistant layer on the side disposed toward the workpiece;

feeding high frequency pulses to the transducer coil;

generating ultrasound signals with the transducer coil;

damping parasitic ultrasound-wave excitations with an insulating layer and an electrically conductive layer, wherein the insulating layer and the electrically conductive layer form an intermediate part, and wherein the intermediate part is disposed between the transducer coil and said front face of the magnet system, and wherein the intermediate part is associated with the transducer coil, wherein the intermediate part is solidly connected to said front face via its insulating layer and with the transducer coil adjoining at the electrically conductive layer via a plastic support mass, and wherein the thickness of the material of the electrically conductive layer is larger than the skin depth of an electromagnetic field for a given high-frequency of the electromagnetic field; and receiving a reflected signal from the workpiece with a separate receiver coil.

* * * * *